United States Patent [19]

MacWhinnie et al.

[11] Patent Number: 5,304,215
[45] Date of Patent: Apr. 19, 1994

[54] THERMAL HEAT PACK FOR BREAST

[76] Inventors: Virginia MacWhinnie; John V. MacWhinnie, both of R.R. 519-Deerfield Rd., Water Mill, N.Y. 11976

[21] Appl. No.: 995,509
[22] Filed: Dec. 21, 1992
[51] Int. Cl.⁵ .............................................. A61F 7/00
[52] U.S. Cl. ..................... 607/106; 450/36; 2/14
[58] Field of Search ............... 128/399, 400, 402, 403, 128/379, 380; 450/38, 56, 57, 58; 363/901; 623/7, 8; 602/14; 607/106, 109, 110; 2/267, 268

[56] References Cited

U.S. PATENT DOCUMENTS

| 2,049,723 | 8/1936 | Pomeranz | 128/402 |
| 3,830,676 | 8/1974 | Elkins | 128/403 X |
| 5,086,771 | 2/1992 | Molloy | 128/402 X |
| 5,133,348 | 7/1992 | Mayn | 128/403 |

FOREIGN PATENT DOCUMENTS 697820  9/1940  Fed. Rep. of Germany ...... 128/403

Primary Examiner—Richard J. Apley
Assistant Examiner—Beverly A. Meindl
Attorney, Agent, or Firm—Alfred M. Walker

[57] ABSTRACT

The present invention relates to a thermal heat pack for heating the female breast during post partum nursing and, more particularly, to a thermal heat pack which readily conforms to the contours of different sized female breasts to provide therapeutic heat to an adjacent breast to reduce swelling and irritation.

9 Claims, 3 Drawing Sheets

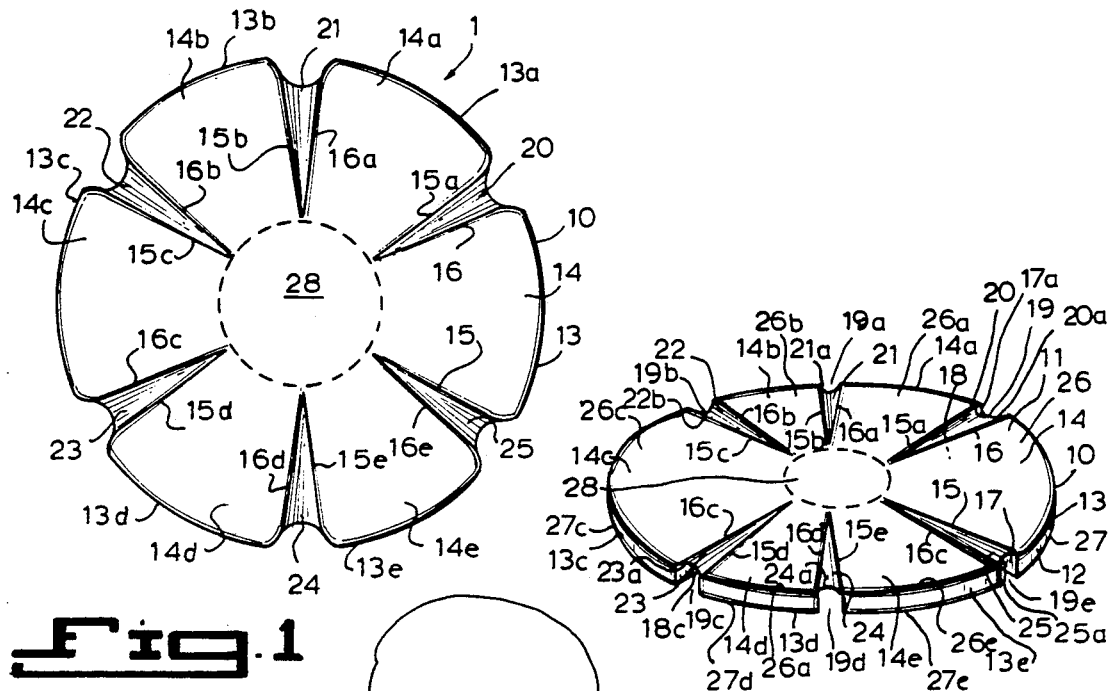
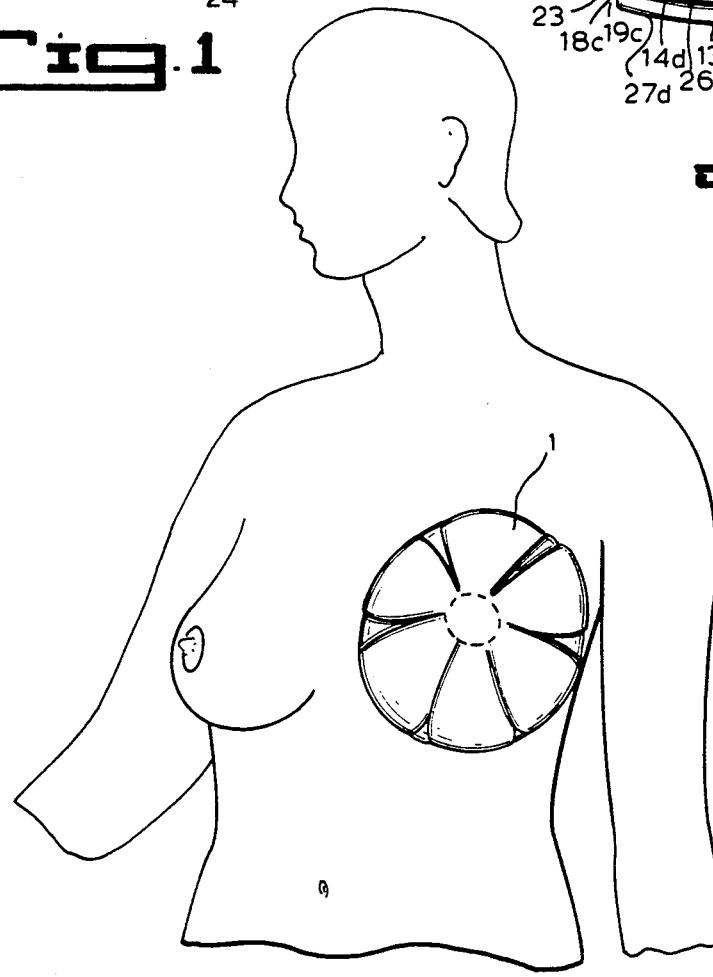
Fig. 1
Fig. 2
Fig. 3

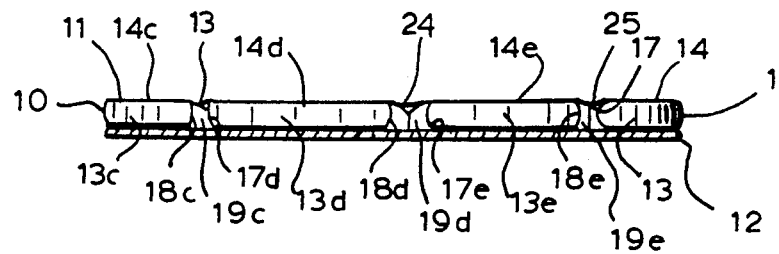
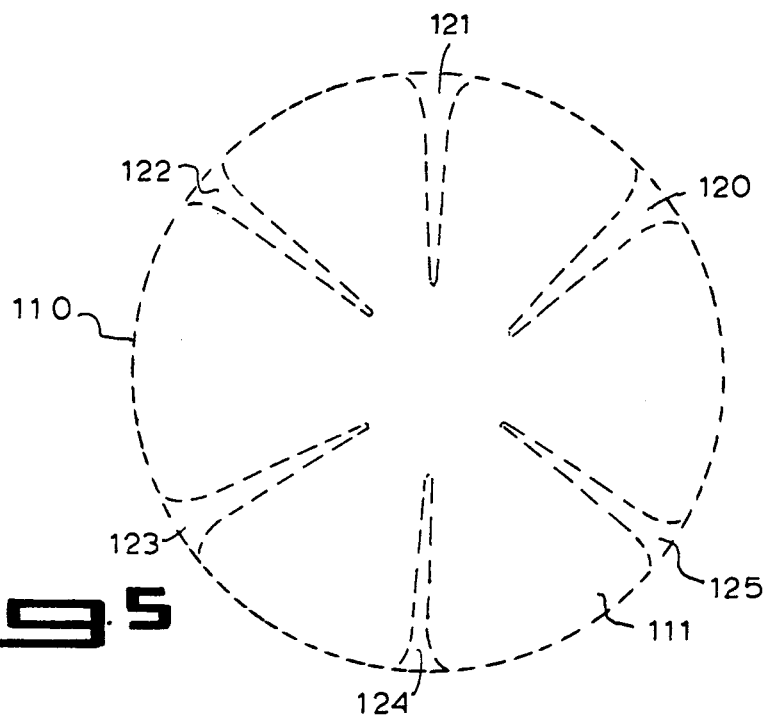
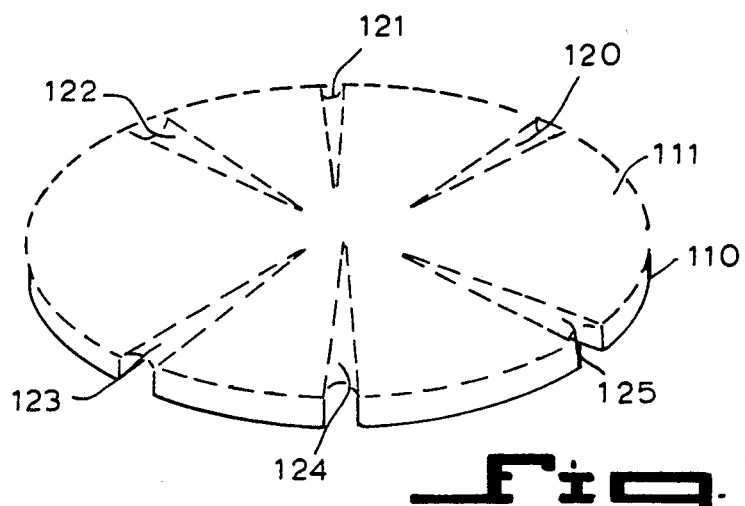

THERMAL HEAT PACK FOR BREAST

BACKGROUND OF THE INVENTION

The present invention relates to a thermal heat pack for heating the female breast during post partum nursing and, more particularly, to a thermal heat pack which readily conforms to the contours of different sized female breasts to provide therapeutic heat to an adjacent breast to reduce swelling and irritation.

A number of cup shaped thermal heat packs are known in the prior art in which thermal heat is provided through a heat pack to provide a therapeutic heat to the human body. Examples of this type of heat pack are shown in U.S. Pat Nos. Re 14,024 of Whitmarsh, 2,298,361 of Freund, 3,500,832 of Nunnery, and 5,050,595 of Krafft. Moreover, U.S. Pat. No. 3,995,621 of Fletcher discloses a liquid cooled brassiere used with diagnostic mammography. Other brassiere patents in general are disclosed in U.S. Pat. No. 2,853,077 of Hunau and 3,430,632 of James. Heat packs in general are disclosed in U.S. Pat. Nos. 3,780,537 of Spencer and 4,846,176 of Golden. Furthermore, U.S. Pat. No. 3,897,821 of Lerner describes a swimming garment wherein breast shaped cups are formed from flat sheets having a V-shaped cut in the sheets.

These patents are incorporated by reference herein for teaching devices in which breast shaped cups are provided for therapeutic use or otherwise.

The above prior art devices have many disadvantages. Typically the devices include cup shaped portions which do not conform closely to various sizes of the breast. If the heat pack does not snugly fit the breast once in position, the heat pack may be too tight or too loose to optimize heating resulting in uneven application of heat to the breast.

The present invention overcomes the aforementioned disadvantages of the prior art by providing a radially bendable thermal heat pack unit. The present invention provides a thermal heat pack which is configured to conform to various sizes and the general shapes of the female breasts to which it is to be applied. Thus the present invention overcomes the disadvantages of the prior art by providing a thermal heat pack unit which conforms to the contour of various sizes and shapes of the female breast with a layered disk with equidistant wedge shaped webs to permit various sized rounded conical cups. Further, the present invention also provides another breast shaped heat pack which is formed from radially extending crescent shaped portions.

Although the Freund, Nunnery and Krafft prior art thermal pack units provide cup shaped heat packs, the prior art devices do not increase or decrease in size for various sized breasts. It is necessary to provide various sizes of specific heat packs to include the wide range of female breast sizes. Consequently, it would be required to have different heat packs for different sizes per breast.

The present invention overcomes the disadvantages of the prior art and provides a simple, pliable, light weight thermal heat pack which readily conforms to the contours of any sized female breast to provide therapeutic heat to the adjacent breast areas.

BRIEF SUMMARY OF THE INVENTION

The present invention provides a thermal heat pack which readily conforms to the contours of various sized female breasts to therapeutically heat adjacent skin areas of the breast. The heat pack has a flattened cylindrical conforming disk of heat conductive material which can be adapted to conform to any sized contour of the female breast.

The heat conductive material may be a heat conductive medium, or a cooling medium.

Further, the present invention includes a thermal heat pack including a round centrally located conformable member with radially extending segments separated by tapered apertures, to conform various sized female breasts. In the preferred embodiment, the tapered apertures are spanned by tapered webs.

Finally, the heat pack includes a moist heat conductive foundation surface, such as terry cloth, separating the heat pack and the breast.

In the preferred embodiment, the heat conductive material includes a conventional heat conductive medium within a pliable outer material. The outer material is fixed about its perimeter to an adjacent conductive material, so that the heat pack directly contacts with the female breast. This provides for an efficient heat transfer between the thermal heat pack and the female breast.

In addition to containing the heating medium fluid, the present invention also acts to cover the adjacent skin portions of various sized breasts.

In a further embodiment, the conforming member is made of a heat conductive material with crescent shaped segments, which is capable of readily conforming to the shape of various sized female breasts.

The thermal heat pack of the present invention uses conventional thermal gel to heat a pliant flattened cylindrical component which changes form and corresponds to the form of the female breast being covered. It is pliant and it flexes over the surfaces of the breast. The heat pack encompasses a flexible foundation member, which is generally circular, attached to a generally cylindrical gel pack, wherein the gel pack is divided into radially extending segmented pockets separated by tapered collapsible joints, such as webs, which taper inward toward a common center portion.

BRIEF DESCRIPTION OF THE DRAWING

FIG. 1 is a top plan view of the thermal heat pack of the present invention.

FIG. 2 is a perspective view of the thermal heat pack of FIG. 1.

FIG. 3 is a perspective view of the thermal heat pack of the present invention applied to a female breast.

FIG. 4 is a side elevational view of the thermal heat pack as in FIG. 1.

FIG. 4A is a sectional side elevational view of the thermal heat pack for the female breast of the present invention as in FIG. 1.

FIG. 5 is a top plan view of the thermal heat pack of another embodiment of the present invention.

FIG. 6 is a perspective view of an alternative embodiment of the device as shown in FIG. 5.

DESCRIPTION OF THE PREFERRED EMBODIMENT

Figure 7:
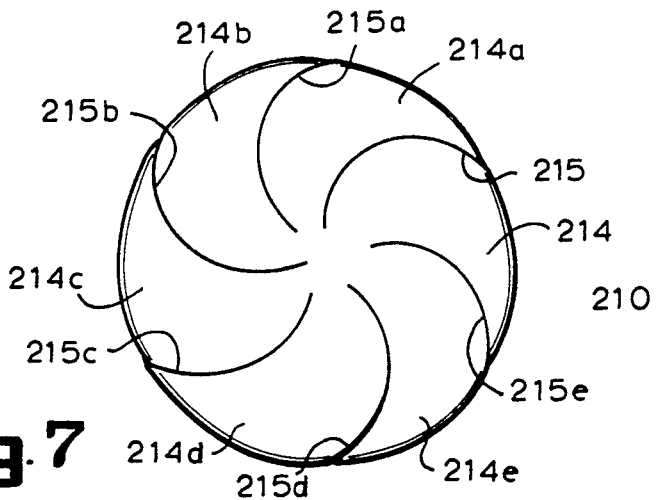
FIG. 7 is a top plan view of a further alternative embodiment of the heat pack of the present invention.

As shown in FIGS. 1-4, the present invention includes a thermal heat pack 1, including a generally flattened cylindrical conforming member 10, having a segmented top surface 11 corresponding to a segmented bottom surface 12 and plurality of upwardly extending convex, circumferential edge walls 13, 13a, 13b, 13c, 13d, 13e, etc.

The conforming member 10 of heat pack 1 includes a plurality of generally triangular segmented pocket members 14, 14a, 14b, 14c, 14d, 14e, etc. which are joined to a common, central portion 28. Each of the triangular separated pocket members 14, 14a, 14b, 14c, 14d, 14e are spaced apart from, and separated from, two adjacent pocket members by tapered apertures. While the apertures may be open, in a preferred embodiment, each triangular pocket member 14, 14a, 14b, 14c, 14d, 14e, etc. is joinable to each said adjacent triangular separated pocket member by tapered flexible joining material units 20, 21, 22, 23, 24, 25 etc., such as webs.

Figure 9:
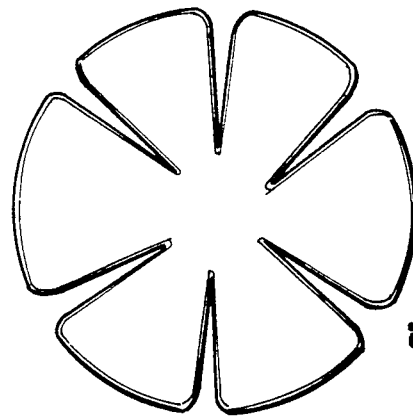
FIG. 9 is a top plan view of another embodiment wherein there are no webs between the triangular segmented portion.
Figure 9A:
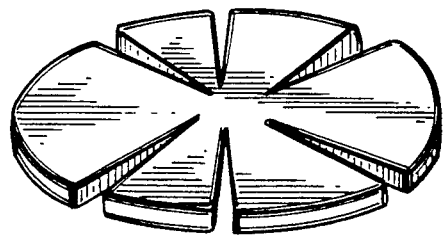
FIG. 9A is a perspective view of the device as in FIG. 9.

For example, as shown in FIG. 1, triangular pocket member 14 is separated from adjacent triangular segmented members 14a and 14e, respectively, by tapered apertures 19, 19e, and preferably joined by webs 20 and 25 respectively. In contrast, FIGS. 9 and 9A depict a web-less embodiment with just apertures between the segments Each segment 14 has opposite edges 15 and 16, from which extend downward non-parallel, extending walls 17 and 18, which also extend up from bottom 12 of heat pack 10.

Segmented member 14 is separated from adjacent segmented members 14a, 14e by tapered apertures 19, 19e, which preferably are covered on one side by flexible joining members, such as webs 20 and 25, respectively. Remaining webs 21, 22, 23, 24, respectively, join other adjacent segmented members of conforming member 10 of heat pack container 1.

Therefore, the thermal heat pack 10 includes hollow cylindrical member 10 with a plurality of equidistant, segmented pockets 14, 14a, 14b, 14c, 14d, 14e, which pockets have respective tops 26, 26a, 26b, 26c, 26d, 26e and respective bottoms, 27, 27a, 27b, 27c, 27d, 27e.

For example, for segmented pocket 14, the two non-parallel, spaced apart flat generally vertical sides 17, 18, bearing top 17 edges 15,16 respectively, extend between the top 26 and the bottom 27 of segmented pocket 14. Each other segment has two non-parallel spaced apart flat generally vertical sides 17a, 18a, etc.

At their respective proximal ends, edges 15, 16 and the two spaced apart non-parallel flat sides 17, 18 converge toward, and intersect with, the common central portion 28 to create a hollow chamber for the even flow of viscous heat conducting material therethrough.

While central portion 28 may be a common point at which radially extending edges 15, 16 meet, in the preferred embodiment shown in FIGS. 1-4, central portion 28 forms a circular, cylindrical member, having a circumferential edge intersected by edges 15, 16,and sides 17, 18, thus truncating the triangular segmented members 14, 14a, 14b, 14c, 14d, 14e, etc. along a further edge contiguous with the circumference of central portion 28.

The non-parallel sides 17, 18, together with edges 15, 16, further diverge at each respective distal end, outward toward, terminate at, and are contiguous with upwardly extending circumferential edges 13, 13a, 13b, 13c, 13d, 13e of generally cylindrical conforming member 10 of the gel heat pack 10. Each generally curved edge 13 forms a part of the outer circumference of conforming member 10.

The non-parallel edges 15, 16 and the flat top surface 11 all initially lie within a common plane of the top 26 of truncated triangular segment 14.

The conforming member 10 further includes the plurality of tapered spaced apart apertures 19, 19a separating the segmented pockets 14, etc. The segmented pockets 14, 14a, 14b, 14c, 14d, 14e have the common central portion 28 extending therebetween. The tapered apertures 19, 19a etc. permit the flexible heat pack to assume various sized domed shapes upon different sized female breasts, since the movement of the edge wall 17 of segment 14 toward adjacent edge wall 18e of segment 14e causes adjacent flat tops 26 and 26e to move from a common plane in two dimensions to a plurality of intersecting planes in three dimensions.

Thus, when the edges of the tapered apertures 19, 19a, 19b, 19c, 19d, 19e are moved toward each other, thereby collapsing flexible webs 20, 21, 22, 23, 24, 25, the heat pack 10 assumes a variable three-dimensional cup shape. For larger sized breasts, the edges 15, 16a, etc. are not moved completely together.

Therefore, as shown in FIG. 3, the tapered apertures 18, 18a, 18b, 18c, 18d, 18e serve for placing the foundation member and the cylinfrical conforming member 10 of heat pack upon the breast, and for maintaining the configuration of the heat pack 1 relative to the corresponding contour of the breast, depending upon the desired size.

The tapered segmented portions 14, 14a, 14b, 14c, 14d, 14e are in fluid flow communication with the common central portion 28 for providing a chamber for even heat distribution of a heating or cooling medium to traverse throughout the heat pack 1.

The common central portion 28 permits flow of the conventional heat conductive material, such as a heat imparting medium or a cooling medium, such as a gel fluid, throughout each of the segmented pockets 14, 14a, 14b, 14c, 14d, 14e, etc. to insure even flow of the gel fluid and even distribution of the heat or coolness imparted to the afflicted breast.

As noted before, because the separations 19, 19a, 19b, 19c, 19d, 19e between the segmented pockets 14, 14a, 14b, 14c, 14d, 14e are tapered, the segmented pockets assume a generally domed cup shape, as the outside widest points of the separations 19, 19a, 19b, 19c, 19d, 19e are closed upon each other.

In a further embodiment, the thermal heat pack utilizes crescent shaped segmented pockets, which assume a generally domed shape, as the outer edges of the crescent segments overlap each other.

Moreover, the tapered apertures 19, 19a, 19b, 19c, 19d, 19e, preferably have radially extending webs 20, 21, 22, 23, 24, 25 radially extending from central portion 28, and tapering outward toward the circumferential edge of heat pack 10. The webs 20, 21, 22, 23, 24, 25 end at common edge points 20a, 21a, 22a, 23a, 24a, 25a at the outer edge of central portion 28.

As shown in FIGS. 5-6 in another embodiment, the webs 120, 121, 122, 123, 124, 125 of heat pack 110 are integral with top portion 111, generally terry cloth, or a bottom sleeve portion (not shown).

Figure 8:
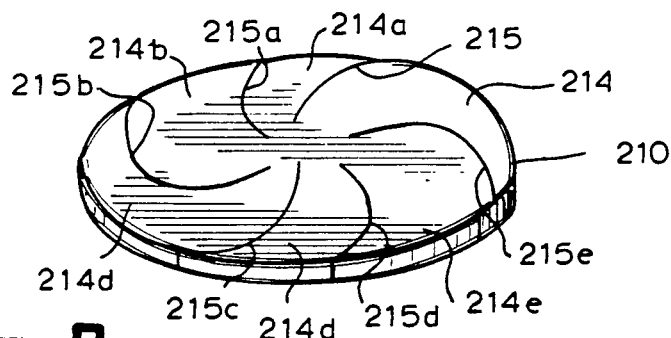
FIG. 8 is a perspective view of the device as in FIG. 7.

In another embodiment as shown in FIGS. 7 and 8, heat pack 210 includes crescent shaped segments 214, 214a, 214b, 214c, 214d, 214e, which are removably adjacent to each other by curved edge cuts 215, 215a, 215b, 215c, 215d, 215e, 2125f. As the crescent segments separate from each other, they permit the central portion 225 to ascend upward to assume a cup shape.

Referring again to the preferred embodiment as shown in FIGS. 1-4, thermal heat pack 10 includes a foundation bottom member 12 which is placed against the breast. As is apparent from FIGS. 1 and 4, foundation bottom member 12, such as terry cloth, corresponds to the exact contour of the breast to provide a uniform heat across the breast. Further, thermal heat pack 10 flexes to adapt to accept the skin.

When in use, the thermal heat pack 10 is placed against the breast with the foundation bottom 12 placed against the breast. The flexible thermal heat pack 10 flexes to the general shape of the breast to assist in keeping the heat pack 10 over the breast.

With the aforegoing description of the present invention and the operation thereof, it will be obvious to those skilled in the art that various modifications can be made to the present invention without departing from the spirit and scope of the present invention which is limited only by the appended claims.

It is noted that other modifications may be made to the present invention, without departing from the spirit and scope of the appended claims.

We claim:

1. A thermal heat pack adapted to closely correspond to the contours of various sized female breasts to heat the adjacent skin area; said thermal heat pack comprising:
    a generally flattened cylindrical conforming member;
    a bottom foundation member forming one side of said thermal heat pack;
    said flattened cylindrical conforming member including a plurality of generally triangular segmented portions radiating from a common central portion within said flattened cylindrical conforming member;
    said conforming member including pliant heat conducting material, said heat pack capable of corresponding to the contour of said breast, such that said bottom foundation member is removably adjacent to said breast, thus permitting uniform application of heat to said breast,
    wherein said conforming member further comprises a plurality of tapered separations between each paid of said adjacent triangular segmented portion; each said adjacent triangular segmented portions being spaced apart from adjacent said triangular segmented portions and,
    each said triangular segmented portion includes at least two non-parallel walls and a generally curved outer wall extending about a portion of a circumference of said conforming member of said heat pack; and
    said heat pack defining a fluid flow chamber therebetween; said chamber including a plurality of segmented recesses positioned within said heat pack for the circulation of the said pliant heat conducting material within said heat pack.

2. The thermal heat pack of claim 1 wherein said cylindrical conforming member includes said bottom foundation membering being mounted to said conforming member.

3. The thermal heat pack of claim 1 wherein said thermal heat pack further comprises said foundation member being mounted to conforming member to form a container therebetween for the circulation of the second heat conductive material;
    said segmented portions being interconnected such that said fluid traverses substantially the entire interior area of said heat pack.

4. The thermal heat pack of claim 1, wherein each pair of said tapered separations are traversed by at least one web of a plurality of tapered webs.

5. The thermal heat pack as defined in claim 1, wherein said generally triangular segmented portions comprise a plurality of equidistant, radially extending truncated segmented portions, each said portion connected by at least one of said plurality of tapered webs.

6. The thermal heat pack as in claim 1 wherein said heat conductive material is a heat imparting medium.

7. The thermal heat pack as in claim 1 wherein said heat conductive material is a cooling medium.

8. The thermal heat pack as in claim 1 wherein
    said central portion bears a circular shape and said central portion has an outer circumference, and further wherein
    each said triangular segmented portion comprises a pair of first and second edges,
    said first and second edges connected at one distal end by a third, curved edge,
    said first and second edges converging toward, and intersecting at a proximal end with said circumference of said central portion,
    said triangular segmented portions each further bearing a fourth edge continuous with a portion of said central portion,
    said fourth edge lying between said first and second edges.

9. A thermal pack for application to a female breast for therapeutic application of heat or cold to the breast, the thermal pack being
    adjustable for varying breast sizes; and the thermal pack further being substantially flat when not in use; and further being
    capable of flexibly changing shape to conform to the contours of the female breast when in use, said thermal pack comprising:
    a substantially disk-shaped conforming member having a thickness with at least one sealed cavity disposed therein; said disk shaped conforming member having a non-continuous circumferential perimeter edge including a plurality of convex edges, each said convex edge spaced apart from adjacent convex edges;
    the disk-shaped conforming member having an inner side and an outer side, the inner side facing the skin of the female breast when the thermal pack is in use;
    the disk-shaped conforming member being made of a suitably pliable bendable material capable of conducting heat and cold; and further wherein
    the disk-shaped conforming member having selectively positioned indentations in said conforming member to permit said disk-shaped conforming member to assume a substantially conforming cup shape when applied to a female breast; and further wherein
    said disk shaped conforming member further comprising a plurality of tapered, triangular pocket members, each said triangular pocket member including two radially extending, non-parallel walls perpendicular to a plane of said disk-shaped conforming member, each said two radially extending, non-parallel walls joined by one of said convex edges, each said pocket member separated and spaced apart from adjacent pocket members by two of said indentations;

said inner side of said disk-shaped conforming member having a moist heat conductive foundation surface suitably attached to said inner side, the moist heat conductive foundation surface forming a layer disposed adjacent to the inner side of said disk-shaped conforming member;

said at least one sealed cavity disposed within the disk-shaped conforming member containing means for retaining and conducting heat; and said at least one sealed cavity disposed within the disk-shaped conforming member containing means for retaining and conducting cold, wherein:

the means for retaining and conducting heat and cold is a thermal gel, said gel being flexible for permitting the disk-shaped conforming member to flexibly change shape to conform to the contours of the female breast; and further wherein said gel is in contact with said disk-shaped conforming member;

said gel is substantially evenly distributed throughout said at least one sealed cavity;

said moist heat conductive foundation surface being comprised of a material suitable for contact with human skin;

said selectively positioned indentations in said disk-shaped conforming member being disposed so as to project radially from a central portion of said disk shaped conforming member in a direction substantially toward the outer, circumferential perimeter edge of said disk-shaped conforming member;

said indentations being a plurality of indentations, said indentations being substantially evenly distributed over said disk shaped conformable member, and being substantially equidistantly distributed from said central portion of said disk shaped conforming member, and, said central portion being in fluid flow communication with said triangular pocket portions.

* * * * *